United States Patent [19]
Lavallée

[11] Patent Number: 6,046,326
[45] Date of Patent: Apr. 4, 2000

[54] PREPARATION OF TRIS(2-HYDROXYETHYL)ISOCYANURATE (THEIC)

[75] Inventor: François A. Lavallée, Fort Wayne, Ind.

[73] Assignee: Essex Group, Fort Wayne, Ind.

[21] Appl. No.: 09/021,160

[22] Filed: Feb. 10, 1998

[51] Int. Cl.[7] .................................................. C07D 251/30
[52] U.S. Cl. ............................................................ 544/221
[58] Field of Search ............................................. 544/221

[56] References Cited

U.S. PATENT DOCUMENTS

| | | | |
|---|---|---|---|
| 3,088,948 | 5/1963 | Little et al. | 260/248 |
| 3,194,810 | 7/1965 | Formaini et al. | 260/307 |
| 3,448,084 | 6/1969 | Burdick et al. | 260/75 |
| 4,444,845 | 4/1984 | Dünwald | 428/422.8 |
| 4,446,300 | 5/1984 | Mabrey et al. | 528/288 |
| 4,474,951 | 10/1984 | Pope | 536/95 |
| 4,849,465 | 7/1989 | Lindvay et al. | 524/736 |

OTHER PUBLICATIONS

Lobova et al. SU 1313855. Chemical Abstract 109: 54792x, 1998.

Tris(2–hydroxyethyl)isocyanurate. JP 8181,571. Chemical Abstract 96: 6762d, 1982.

Tris (2–hydroxyethyl) Isocyanurate 2 Technical Data Bulletins from Allied Chemical Corp., all pages.

Sayigh and H. Ulrich, "Tris (2–hydroxyethyl) Isocyanurate" *J. Chem. Soc.*, 3148–49 (1961).

Thomas C. Frazier, Edwin D. Little and Billy E. Lloyd, "Isocyanurates. I. Some Condensation Reactions of Cyanuric Acid" 25 *J. Org. Chem.*, 1944–46 (1960).

Richard W. Cummins, "Reaction of Cyanuric Acid with Epoxides" 28 *J. Org. Chem.*, 85–89 (1963).

Chiron–Charier, P. Caubére, "Application Of Reactivity Of Alkaline Salts Of Isocyanuric Acid To The Synthesis Of Mono And Trisubstituted Isocyanurates" 23 (19) *Synthetic Communiations*, 2659–72 (1993).

*Primary Examiner*—Richard L. Raymond
*Assistant Examiner*—V. Balasubramanian
*Attorney, Agent, or Firm*—Rader, Fishman & Grauer PLLC

[57] ABSTRACT

A method of preparing tris(2-hydroxyethyl)isocyanurate (THEIC) is disclosed. The method comprises the step of heating a mixture of ethylene carbonate and isocyanuric acid in the presence of a catalyst at a temperature between about 160° C. and 170° C. The molar ratio of ethylene carbonate to isocyanuric acid is at least about 3 to 1, and the catalyst has at least one amine functional group. THEIC produced by the disclosed method can be used without purification as a cross-linking agent in polyester-based magnet wire enamels.

22 Claims, 2 Drawing Sheets

PREPARATION OF TRIS(2-HYDROXYETHYL)ISOCYANURATE (THEIC)

FIELD OF THE INVENTION

This invention pertains to a method for producing tris(2-hydroxyethyl)isocyanurate (THEIC).

BACKGROUND OF THE INVENTION

Tris(2-hydroxyethyl)isocyanurate (THEIC) is a triol used extensively to improve the performance of polyester-based magnet wire enamels. Electrical insulation made with THEIC polyesters of adipic, phthalic, isophthalic, terephthalic and similar polyacids exhibit good dielectric properties, and show improved adhesion, flexibility, heat shock, and heat aging performance.

THEIC is commercially prepared by reacting isocyanuric acid with ethylene oxide in an inert solvent and in the presence of an alkaline catalyst (normally an alkali metal hydroxide). Although good yields are obtained, the method is not without problems. Ethylene oxide, which is a gas at room temperature and pressure, is an acute and chronic poison, as well as an explosive hazard, and therefore difficult to handle safely. Furthermore, the reaction product must be purified before it can be used in a magnet wire enamel. Impurities (especially cations) will increase the electrical conductivity of the electrical insulation, and may also interfere with formation of the polyester and contribute to premature decomposition of THEIC.

Purification is an involved process. First, the solid catalyst and any metal salt by-products are removed by filtration. Next, the filtrate is distilled under vacuum to separate out the inert solvent, leaving a viscous residue (THEIC). Finally, the THEIC is re-dissolved in a volatile organic solvent and then recrystallized yielding THEIC sufficiently pure for use in magnet wire enamel.

It is therefore desirable to prepare THEIC without the handling problems associated with ethylene oxide, and without the need for extensive purification of the reaction product prior to its use.

SUMMARY OF THE INVENTION

In accordance with one aspect of the present invention, there is provided a method of making tris(2-hydroxyethyl)isocyanurate. The method comprises the step of reacting ethylene carbonate with isocyanuric acid in the presence of a catalyst in which the molar ratio of ethylene carbonate to isocyanuric acid is at least about 3 to 1, and the catalyst has at least one amine functional group.

In accordance with a second aspect of the present invention, there is provided a method of making tris(2-hydroxyethyl)isocyanurate, which comprises the step of heating a mixture of ethylene carbonate and isocyanuric acid in the presence of a catalyst at a temperature between about 160° C. and 170° C. The molar ratio of ethylene carbonate to isocyanuric acid is at least about 3 to 1, and the catalyst has at least one amine functional group.

DETAILED DESCRIPTION OF THE PREFERRED EMBODIMENTS

Ethylene carbonate can be reacted with isocyanuric acid to form tris(2-hydroxyethyl)isocyanurate (THEIC) in accordance with the reaction scheme in equation I:

$$3C_3H_4O_3 + C_3N_3O_3H_3 + \text{Catalyst} \rightarrow C_3N_3O_3(CH_2CH_2OH)_3 + 3CO_2\uparrow + \text{Catalyst} \quad \text{I}$$

Good yields of THEIC can only be obtained if a proper catalyst is used.

Amine catalysts are especially useful for the production of THEIC used in polyester-based, magnet wire insulation. Amines are generally not easily ionized and therefore do not degrade the dielectric properties of the insulation. Furthermore, most amines are relatively weak bases and therefore do not substantially interfere in the acid-catalyzed formation of the polyester. Thus, unlike the metal hydroxide catalysts employed in commercial THEIC production, amine catalysts typically do not need to be removed prior to preparing a THEIC polyester.

Numerous amines were screened for catalytic activity. Each amine was evaluated by reacting ethylene carbonate and isocyanuric acid in the presence of the amine. The reaction mixture was prepared in accordance with the materials and amounts listed in Table 1. Ethylene glycol comprised about 20 percent of the reaction mixture and served as a non-reactive solvent. Each reaction mixture was held at a temperature between 165° C. and 170° C. until the evolution of $CO_2$ stopped or until the reaction had proceeded for 8 hours, whichever period was shorter. The weight of evolved $CO_2$ was measured by weighing the reaction flask and its contents before and after reaction. The reaction mixtures were allowed to cool overnight at room temperature. The best catalysts were those that produced, upon cooling, a large number of substantially colorless crystals in about 24 hours.

Figure 1:
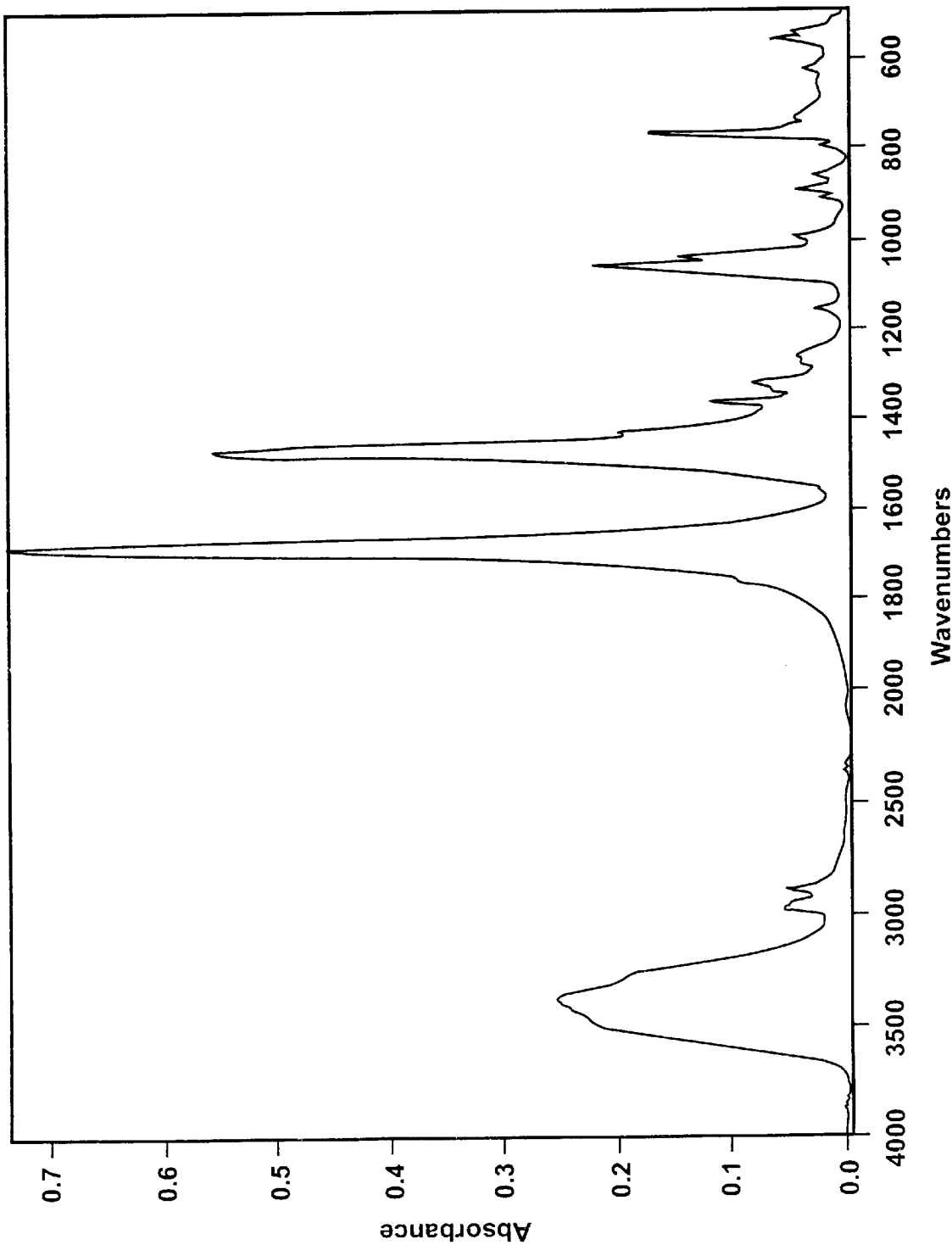
FIG. 1 shows an IR spectrum of the product obtained by reacting isocyanuric acid and ethylene carbonate in the presence of benzotriazole.
Figure 2:
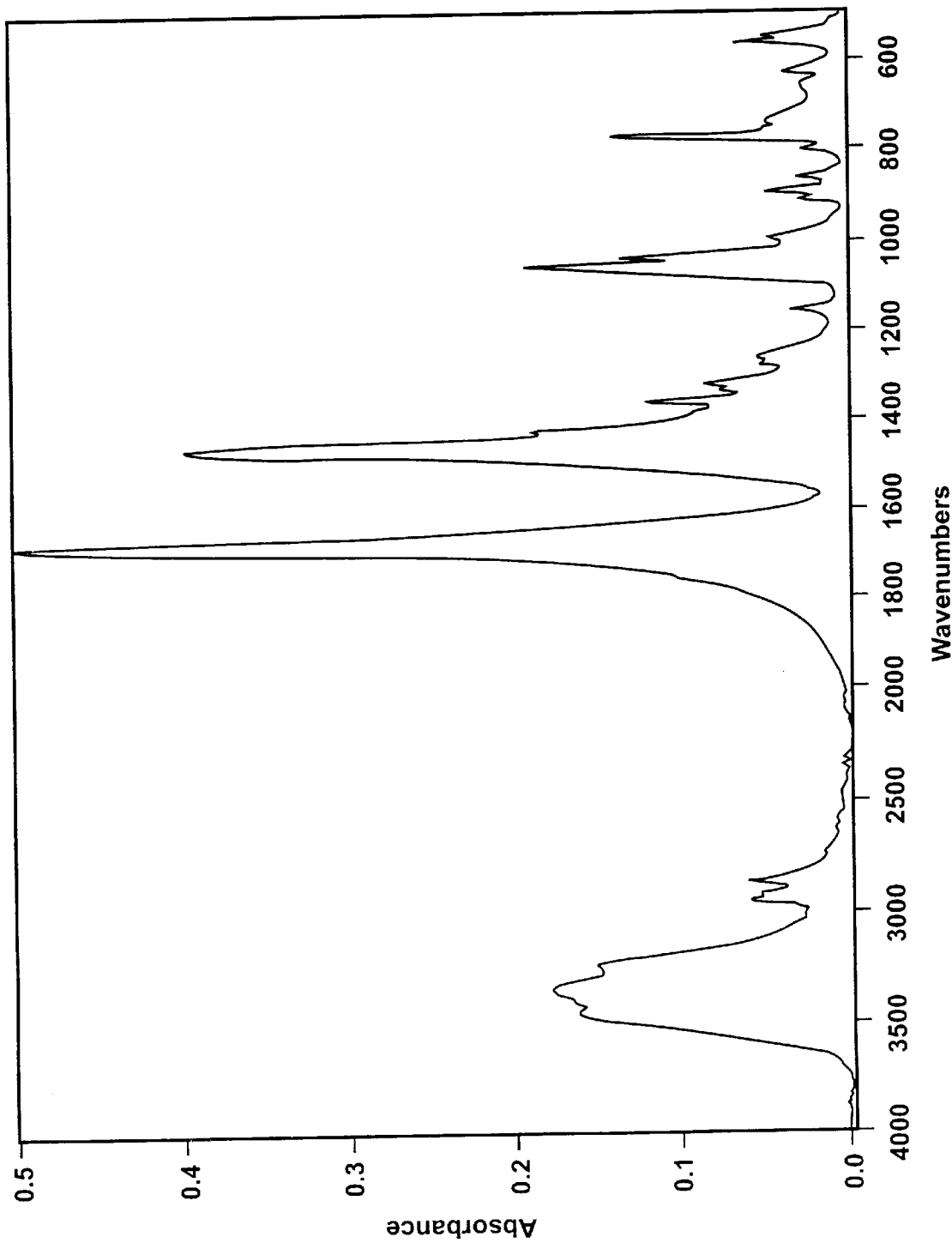
FIG. 2 shows an IR spectrum of commercially available THEIC.

THEIC was identified by IR spectrum analysis and melting point determination. FIG. 1 shows an IR spectrum of the product obtained by reacting isocyanuric acid and ethylene carbonate in the presence of benzotriazole, while FIG. 2 shows an IR spectrum of commercially available THEIC. Comparing the two IR spectra shows that the benzotriazole-catalyzed reaction product is THEIC. Likewise, comparing melting points shows good agreement between the benzotriazole-catalyzed THEIC and commercially available THEIC. For example, benzotriazole-catalyzed THEIC (unpurified) exhibits a melting range of 133.5° C. to 135.0° C., while commercially available THEIC, spiked with 2 percent ethylene carbonate to approximate the reaction conditions shown in Table 1, exhibits a melting range of 133.0° C. to 134.5° C. Moreover, when recrystallized, the benzotriazole-catalyzed THEIC has a melting point of 137° C., while commercially available THEIC has a melting range of 136° C. to 140° C.

Table 2 illustrates the range of amine catalysts tested. The amines evaluated can be classified as aniline derivatives (N-substituted aniline); benzyl-alkyl amines; aliphatic amines; 5- and 6-member heterocycles containing at least one amine functional group; heterocycles consisting of fused 5- and 6-member rings; tetramines; and quarternary ammonium salts. Secondary, tertiary, and in one case, primary amines were represented within each class.

In Table 2, a qualitative measure of catalytic activity is given by the relative quantity and appearance of the reaction product upon cooling. The presence of "solid" material in the reaction flask means that following completion of the reaction (marked by the end of $CO_2$ evolution), the reaction product had gone from a clear solution to a crystalline mass within about 24 hours. In contrast, the presence of a "slurry" upon cooling means that the material in the reaction flask looked identical to the starting materials, indicating insufficient conversion of the starting materials and poor catalytic activity. "Part crystalline" indicates that there was substantial, though incomplete conversion of the starting materials. Finally, "clear liquid" indicates that ethylene carbonate and isocyanuric acid were consumed without the appearance of THEIC crystals. This suggests, as discussed below, that THEIC may have formed and decomposed.

Of the amines tested, benzotriazole performed the best. In all cases, the use of benzotriazole resulted in the expected amount of evolved $CO_2$, and in a flask full of nearly colorless THEIC crystals. Other amines performed nearly as well. For example, the 6-member heterocycles (3-methylpiperidine and 3-ethylpyridine) also resulted in good crystal formation, though the amount of evolved $CO_2$ was slightly below the theoretical yield. Note that in all cases tested, the presence of cresol (a common constituent in polyesterifications) decreased the evolution of $CO_2$ by about 50%, and is considered detrimental to the formation of THEIC by the reaction scheme in equation I. Dibutyltin Oxide (DBTO), a common esterification catalyst is also detrimental to the formation of THEIC.

As discussed above it is thought that, in some cases, THEIC was formed but decomposed. For example, two of the benzyl-alkyl amines, most of the fused 5- and 6-member ring heterocycles, and the quarternary ammonium salt tetraethylammonium bromide, all yielded the expected amount of $CO_2$, but produced no crystals within 24 hours of reaction (though in some cases, crystals formed within about a week). Hexamethylene tetramine did produce a potentially usable polyester, although the post reaction solution was too dark to determine the extent of reaction based on the amount of crystalline material.

Because it is well known that THEIC will decompose to 2-oxazolidone at about 180° C., it was necessary to determine whether the amine catalyst would also catalyze the decomposition of THEIC. To evaluate its catalytic decomposition, commercially available THEIC, along with ethylene glycol and the amine to be tested, were added to a flask in the amounts listed in Table 3. The reactants were thoroughly mixed, and then placed in a 165° C. oven for about 8 hours. After removal from the oven the reaction mixture was allowed to stand for about 24 hours at room temperature. The mixture was then compared to a control mixture that had been similarly heated, but contained only THEIC and ethylene glycol.

Table 4 shows the results of the experiments on catalytic decomposition of THEIC. As expected, the flask containing no amine yielded abundant THEIC crystals upon cooling, indicating that little or no THEIC had decomposed. Similarly, benzotriazole did not appear to catalyze the decomposition of THEIC. Aniline and 5-methyl-1H-benzotriazole also appeared to catalyze little decomposition of THEIC. Most of the other amines tested apparently catalyzed the decomposition of THEIC as evidenced by the lack of a significant amount of crystals within the 24 hour cooling period.

Based on the results in Table 2 and Table 4, benzotriazole appears to be the most effective catalyst since it accelerates the formation, but not the decomposition of THEIC. Because of the potential for decomposition at high temperatures (about 180° C. or above), the reaction given by equation I should be carried out at the lowest temperature possible that is consistent with short reaction time (about 8 hours or less). When using benzotriazole or amines having similar catalytic activity, the reaction should be carried out at a temperature between about 160° C. and about 170° C.

The preparation of THEIC and polyester-based wire enamels containing THEIC are illustrated in the following examples.

EXAMPLES 1–21

The ingredients in Table 5 were charged to a 500 ml, 3-neck flask equipped with a motor-driven stirrer, a thermometer, a water-cooled condenser, and a temperature controller. With mixing, the ingredients were heated to between 165° C. and 170° C. and were held within that temperature range until the solution stopped bubbling. During the reaction, the time at which the slurry became clear was noted. The condenser was open to the atmosphere to allow for $CO_2$ to escape, and the weight of evolved $CO_2$ was measured by weighing the reaction flask and its contents before and after reaction. After reaction, the reaction product (THEIC) was either used immediately in the manufacture of the polyester-based wire enamel or stored for later use.

THEIC prepared by the above method was incorporated into standard Essex polyester wire enamels in a conventional manner. The THEIC-modified polyester resins were then coated on 18 AWG (0.0404" diameter) copper wire to a build of 2.3–2.7 mils with 7 passes through a 20 ft. vertical tower having a cure zone temperature of 468° C. Following application of the polyester base coat, a thin (0.6–0.8 mil) nylon top coat was added. The resulting insulated wire was a NEMA (1997) MW-76C Heavy magnet wire.

The THEIC-modified polyester enamels exhibited cured properties similar to enamels made with commercially available THEIC. Cure characteristics are listed in Table 6 (low molecular weight polyesters) and Table 7 (high molecular weight polyesters) for various weight ratios of dibutyltin oxide (polyesterification catalyst) to amine (THEIC formation catalyst). Dissipation factor ($D_f$) at 250° C. and 1 kHz, and the glass transition temperature ($T_g$) are presented for three wire speeds. As can be see by examining the data for the benzotriazole runs 5–9, 13–15, and 18, $D_f$ and $T_g$ can be optimized by varying the DBTO/amine ratio. With the exception of run 6, all wire runs exhibited fair or good smoothness or runnability (although smoothness is not necessarily a function of THEIC performance). Cure data was not obtained for the hexamethylene tetramine (HMTA) runs (19 and 20) because the catalyst produced a dark colored insulation. In addition, polyesterifications using HMTA-catalyzed THEIC were very rapid.

As shown in Table 8, insulation performance for high molecular weight polyester enamels made with THEIC prepared by the above method compare favorably with an enamel made with commercially available THEIC. Both enamels made with benzotriazole-catalyzed THEIC (15 and 18) showed no failures in heat shock and Essex snap flexibility testing. In addition, they exhibited good wire adhesion (slit twist adhesion failure at 60 twists or more), demonstrated high dielectric breakdown resistance (greater than 10,000 V), and did not undergo plastic deformation until heated to relatively high temperatures (thermoplastic flow greater than 260° C.).

Preferred embodiments of the present invention have been disclosed. A person of ordinary skill in the art will realize, however, that certain modifications will come within the teachings of this invention. Therefore, the following claims should be studied to determine the true scope and content of the invention.

TABLE 1

| Materials for Testing Catalyst Activity | | | |
| --- | --- | --- | --- |
| Component | Moles | Weight, g | Weight % |
| ethylene carbonate | 4.154 | 365.8 | 54.59 |
| isocyanuric acid | 1.319 | 170.3 | 25.41 |
| ethylene glycol | 2.126 | 132.0 | 19.70 |
| catalyst | | 2.0 | 0.30 |
| total | | 670.1 | 100.00 |

TABLE 2

Catalysts Tested

| Catalyst | Class | Time to Clear hours | Evolved $CO_2$ % Theoretical | Appearance Upon Cooling |
|---|---|---|---|---|
| aniline | N-substituted aniline | >8 | 36 | slurry |
| phenylethylamine | N-substituted aniline | >8 | 42 | slurry |
| diphenylamine | N-substituted aniline | >>5 | not measured | slurry |
| triphenylamine | N-substituted aniline | >5 | 17 | slurry |
| benzylmethylamine | benzyl-alkyl amine | 2.5 | 101 | clear liquid |
| dimethylbenzylamine | benzyl-alkyl amine | 3 | 103 | clear liquid |
| tribenzylamine | benzyl amine | >>5 | 8 | slurry |
| tri-n-octylamine | aliphatic amine | 2¾ | 92 | part crystalline |
| tributylamine | aliphatic amine | 3 | 92 | part crystalline |
| triethanolamine | aliphatic amine | not measured | 42 | slurry |
| imidazole | 5-member heterocycle | 3 | 100 | clear liquid |
| 1H-1,2,3-triazole | 5-member heterocycle | 4 | 35 | clear liquid |
| 3-methylpiperidine | 6-member heterocycle | 4 | 93 | solid |
| 3-ethylpyridine | 6-member heterocycle | 1¾ | 90 | solid |
| indazole | Fused 5- & 6-member ring heterocycle | no measured | 44 | slurry |
| benzimidazole | Fused 5- & 6-member ring heterocycle | 2¼ | 102 | clear liquid |
| benzotriazole | Fused 5- & 6-member ring heterocycle | 5 | 101 | solid |
| benzotriazole w/no glycol | Fused 5- & 6-member ring heterocycle | 5 | 101 | solid |
| 5-methyl-1H-benzotriazole | Fused 5- & 6-member ring heterocycle | 4 | 98 | ½ solid, ½ slurry |
| hexamethylene tetramine | tetramine | 2 | 108 | clear liquid |
| $(C_2H_5)_4N^+Br^-$ | quarternary ammonium salt | 4 | 100 | part crystalline |
| dibutyltin oxide | | >>8 | not measured | slurry |
| potassium carbonate | | 4 | 104 | clear liquid |

TABLE 3

Materials for Testing Catalytic Decomposition of THEIC

| Component | Weight % |
|---|---|
| THEIC | 72.43 |
| ethylene glycol | 27.16 |
| catalyst | 0.41 |
| total | 100.00 |

TABLE 4

Stability of THEIC in Presence of Catalyst at 165° C. for 8 Hours

| THEIC Formation Catalyst | Class | Appearance Upon Cooling |
|---|---|---|
| none (25° C.) | | solid |
| none | | solid |
| aniline | N-substituted aniline | solid (½ of original THEIC crystallized) |
| benzylmethylamine | benzyl-alkyl amine | solid (a few crystals) |
| dimethylbenzylamine | benzyl-alkyl amine | clear liquid |
| tri-n-octylamine | aliphatic amine | solid (a few crystals) |
| tributylamine | aliphatic amine | solid (a few crystals) |
| imidazole | 5-member heterocycle | clear liquid |
| 3-methylpiperidine | 6-member heterocycle | clear liquid |
| 3-ethylpyridine | 6-member heterocycle | solid (a few crystals) |
| benzimidazole | Fused 5- & 6-member ring heterocycle | clear liquid |
| benzotriazole | Fused 5- & 6-member ring heterocycle | solid |

TABLE 5

Materials for Laboratory Preparation of THEIC

| Component | Moles | Weight, g | Weight % |
|---|---|---|---|
| ethylene carbonate | 2.08 | 182.9 | 54.6 |
| isocyanuric acid | 0.66 | 85.1 | 25.4 |
| ethylene glycol | 1.06 | 66.0 | 19.7 |
| catalyst | | 1.0 | 0.3 |
| total | | 335.0 | 100.0 |

TABLE 6

Cured Properties for THEIC-Modified Low Molecular Weight Polyester Base Coat, Nylon Top Coat, 18 AWG Magnet Wire, NEMA (1997) MW-76C Heavy

| Run | Amine Catalyst | DBTO/Amine g/g | $D_f^1$ @ 250° C. & 1 kHz for 3 Wire Speeds | | | Tg, K for 3 Wire Speeds | | | Wire Surface |
|---|---|---|---|---|---|---|---|---|---|
| | | | Low | Med | High | Low | Med | High | |
| 1 | diphenylamine | 1/1 | 0.12 | 0.16 | 0.23 | 413 | 412 | 410 | good |
| 2 | dimethylbenzylamine | 1/1 | | | | 421 | | | good |
| 3 | triethanolamine | 1/1 | 0.14 | 0.19 | 0.28 | 418 | 416 | 418 | good |
| 4 | N-methy-2-pyrrolidinol | 1/1 | 0.08 | 0.09 | 0.20 | 415 | 413 | 411 | good |
| 5 | benzotriazole | 0.4/1 | 0.16 | 0.31 | 0.48 | 424 | 419 | 414 | good |
| 6 | benzotriazole | 1/1 | | | | | | | poor |
| 7 | benzotriazole | 3/1 | 0.09 | 0.17 | 0.19 | 430 | 425 | 422 | fair |
| 8 | benzotriazole[2] | 3/1 | 0.08 | 0.11 | 0.18 | 427 | 424 | 420 | good |
| 9 | benzotriazole | 4/1 | 0.20 | 0.34 | 0.43 | 415 | 410 | 407 | good |
| 10 | $(C_2H_5)_4N^+Br^-$ | 1/1 | | | | 420 | | | good |
| 11 | control | | 0.13 | 0.15 | 0.20 | 414 | 412 | 410 | good |

[1]Measured in accordance with ASTM D-1676-83.
[2]No excess ethylene carbonate.

TABLE 7

Cured Properties for THEIC-Modified High Molecular Weight Polyester Base Coat, Nylon Top Coat, 18 AWG Magnet Wire, NEMA (1997) MW-76C Heavy

| Run | Amine Catalyst | DBTO/Amine g/g | $D_f^1$ @ 250° C. & 1 kHz for 3 Wire Speeds | | | Tg, K for 3 Wire Speeds | | | Wire Surface |
|---|---|---|---|---|---|---|---|---|---|
| | | | Low | Med | High | Low | Med | High | |
| 12 | aniline | 1/1 | | | | | | | poor |
| 13 | benzotriazole | 1/1 | 0.16 | 0.27 | 0.41 | 421 | 414 | 408 | good |
| 14 | benzotriazole | 2.5/1 | 0.26 | 0.38 | 0.58 | 421 | 419 | 415 | good |
| 15 | benzotriazole | 3/1 | 0.13 | 0.20 | 0.30 | 416 | 414 | 408 | good |
| 16 | benzotriazole[2] | 3/1 | 0.05 | 0.16 | 0.17 | 430 | 421 | 420 | fair |
| 17 | benzotriazole[3] | 3/1 | 0.14 | 0.35 | 0.49 | 420 | 413 | 412 | fair |
| 18 | benzotriazole | 4/1 | 0.09 | 0.25 | 0.24 | 424 | 417 | 416 | good |
| 19 | hexamethylene tetramine[4] | 3.75/1 | 0.12 | 0.28 | 0.31 | 429 | 422 | 423 | good |
| 20 | hexamethylene tetramine[4] | 5/1 | 0.22 | 0.33 | 0.38 | 425 | 420 | 419 | fair |
| 21 | control | | 0.10 | 0.18 | 0.23 | 422 | 417 | 415 | good |

[1]Measured in accordance with ASTM D-1676-83.
[2]No excess ethylene carbonate; 3:1 molar ratio of ethylene carbonate to isocyanuric acid.
[3]THEIC prepared at 173° C.
[4]Polyesterifications were very fast.

TABLE 8

Performance of THEIC-Modified High Molecular Weight Polyester Base Coat, Nylon Top Coat, 18 AWG Magnet Wire, NEMA (1997) MW 76C Heavy

| Run | 21 | | | 18 | | | 15 | | |
|---|---|---|---|---|---|---|---|---|---|
| DBTO/Benzotriazole, g/g | control | | | 4/1 | | | 3/1 | | |
| Wire Speed, ft/min | 56 | 61 | 62½ | 56 | 61 | 62½ | 53 | 56 | 59 |
| $T_g$, K | 422 | 417 | 415 | 424 | 417 | 416 | 416 | 414 | 408 |
| $D_f^1$ @ 250° C. & 1 kHz | 0.10 | 0.18 | 0.23 | 0.09 | 0.25 | 0.24 | 0.13 | 0.20 | 0.30 |

TABLE 8-continued

Performance of THEIC-Modified High Molecular Weight Polyester Base Coat, Nylon Top Coat, 18 AWG Magnet Wire, NEMA (1997) MW 76C Heavy

| | | | | | | | | | |
|---|---|---|---|---|---|---|---|---|---|
| Smoothness | −9 | −9 | −9 | 8½ | −9 | −9 | −9 | −9 | −9 |
| Enamel OD, in | 0.0435 | | | 0.0435 | | | | 0.0436 | |
| Bare Wire OD, in | 0.0404 | | | 0.0404 | | | | 0.0404 | |
| Base Coat OD, in | 0.0427 | | | 0.0427 | | | | 0.0430 | |
| Top Coat Build, in | 0.0008 | | | 0.0008 | | | | 0.0006 | |
| Heat Shock[1,2], Failures in 3 Coils | 0, 0, 0 | 0, 0, 0 | 0, 0, 0 | 0, 0, 0 | 0, 0, 0 | 0, 0, 0 | 0, 0, 0 | 0, 0, 0 | 0, 0, 0 |
| Flexibility[3], Failures in 3, 1X Coils | 0, 0, 0 | 0, 0, 0 | 0, 0, 0 | 0, 0, 0 | 0, 0, 0 | 0, 0, 0 | 0, 0, 0 | 0, 0, 0 | 0, 0, 0 |
| Slit Twist Adhesion[4], Twists | 59 | 66 | 71 | 65 | 62 | 65 | 54 | 52 | 63 |
| Dielectric Breakdown[1,5], V | 12,554 | 14,976 | 14,474 | 12,688 | 14,868 | 15,722 | 11,066 | 13,768 | 12,464 |
| Thermoplastic Flow[1,6], ° C. | 268 | 266 | 264 | 272 | 267 | 258 | | 266 | |

[1]Measured in accordance with ASTM D-1676-83.
[2]NEMA 3.4.1.1 (1997) standard test (½ hour at 220° C).
[3]Essex Snap Flexibility: a magnet wire is rapidly elongated to its breaking point and wrapped on 1X diameter forming 3 coils, each having 10 turns per coil; the number of failures (cracks) is reported.
[4]The insulation of a taught magnet wire is slit axially; the number of times the magnet wire can be twisted before the insulation peels off the wire is reported.
[5]NEMA 3.7 (1997) standard test.
[6]NEMA 3.5 (1997) standard test.

I Claim:

1. A method for making tris(2-hydroxyethyl)isocyanurate comprising:

reacting ethylene carbonate with isocyanuric acid in the presence of a heterocyclic amine catalyst, the molar ratio of ethylene carbonate to isocyanuric acid being at least about 3 to 1;

wherein the heterocyclic amine catalyst is a five-member ring, a six-member ring, or a five-member ring ortho-fused to a six-member ring, the heterocyclic catalyst having only carbon and nitrogen ring members, the ring members bonded to none, one, or two substituents independently selected from the group consisting of hydrogen, alkyl, and hydroxyl.

2. The method of claim 1, wherein the five-member ring is an N-alkyl pyrrolidinol, an N-alkyl pyrrolidine, an azole, a diazole or a triazole.

3. The method of claim 1, wherein the six-member ring is an alkyl pyridine or an alkyl piperidine.

4. The method of claim 1, wherein the five member ring ortho-fused to a six-member ring is a benzoazole, a benzodiazole, or benzotriazole.

5. A method of making tris(2-hydroxyethyl)isocyanurate comprising:

reacting ethylene carbonate with isocyanuric acid in the presence of an amine catalyst, the molar ratio of ethylene carbonate to isocyanuric acid being at least about 3 to 1;

wherein the amine catalyst is an N-substituted aniline, an aliphatic amine, benzylamine, dibenzylamine, tribenzylamine, a benzylalkyl amine, a dibenzylalkyl amine, or a tetramine.

6. The method of claim 5, wherein the amine catalyst is an N-substituted aniline.

7. The method of claim 6, wherein the amine catalyst is an N-alkyl aniline, an N-phenyl aniline, or an N,N-alkylphenyl aniline.

8. The method of claim 5, wherein the amine catalyst is a primary aliphatic amine, a secondary aliphatic amine or a tertiary aliphatic amine.

9. The method of claim 5, wherein the amine catalyst is benzylamine, dibenzylamine, tribenzylamine, a benzylalkyl amine, or a dibenzylalkyl amine.

10. The method of claim 5, wherein the amine catalyst is a tetramine.

11. A method of making tris(2-hydroxyethyl)isocyanurate comprising:

heating a mixture of ethylene carbonate and isocyanuric acid in the presence of a heterocyclic amine catalyst at a temperature between about 160° C. and about 170° C., the molar ratio of ethylene carbonate to isocyanuric acid being at least about 3 to 1;

wherein the heterocyclic amine catalyst is a five-member ring, a six-member ring, or a five-member ring ortho-fused to a six-member ring, the heterocyclic catalyst having only carbon and nitrogen ring members, the ring members bonded to none, one, or two substituents independently selected from the group consisting of hydrogen, alkyl, and hydroxyl.

12. The method of claim 11, wherein the ethylene carbonate and isocyanuric acid are dispersed in a polyol.

13. The method of claim 12, wherein the polyol is ethylene glycol; glycerine; pentaerythritol; 1,1,1-trimethylolethane; 1,1,1-trimethylolpropane; sorbitol; mannitol; dipentaerythritol; an aliphatic hydrocarbon diol; or a cyclic glycol.

14. The method of claim 11, wherein the five-member ring is an N-alkyl pyrrolidinol, an N-alkyl pyrrolidine, an azole, a diazole or a triazole.

15. The method of claim 11, wherein the six-member ring is an alkyl pyridine or an alkyl piperidine.

16. The method of claim 11, wherein the five-member ring ortho-fused to a six-member ring is a benzoazole, a benzodiazole, or benzotriazole.

17. A method for making tris(2-hydroxyethyl) isocyanurate comprising:

heating a mixture of ethylene carbonate and isocyanuric acid in the presence of an amine catalyst at a temperature between about 160° C. and about 170° C., the molar ratio of ethylene carbonate to isocyanuric acid being at least about 3 to 1;

wherein the amine catalyst is an N-substituted aniline, an aliphatic amine, benzylamine, dibenzylamine, tribenzylamine, a benzylalkyl amine, a dibenzylalkyl amine, or a tetramine.

18. The method of claim 17, wherein the amine catalyst is an N-substituted aniline.

19. The method of claim 18, wherein the amine catalyst is an N-alkyl aniline, an N-phenyl aniline, or an N,N-alkylphenyl aniline.

20. The method of claim 17, wherein the amine catalyst is a primary aliphatic amine, a secondary aliphatic amine or a tertiary aliphatic amine.

21. The method of claim 17, wherein the amine catalyst is benzylamine, dibenzylamine, tribenzylamine, a benzylalkyl amine, or a dibenzylalkyl amine.

22. The method of claim 17, wherein the amine catalyst is a tetramine.

* * * * *